United States Patent [19]

Schanzlin

[11] Patent Number: 5,092,863
[45] Date of Patent: Mar. 3, 1992

[54] OPHTHALMOLOGICAL SURGERY APPARATUS AND METHODS

[75] Inventor: David J. Schanzlin, St. Louis, Mo.

[73] Assignee: St. Louis University, St. Louis, Mo.

[21] Appl. No.: 506,257

[22] Filed: Apr. 9, 1990

[51] Int. Cl.$^5$ ............................................. A61N 5/06
[52] U.S. Cl. ....................................... 606/5; 606/13; 128/395
[58] Field of Search ................ 606/2, 4, 5, 6, 166; 604/20; 128/395, 362, 793; 219/121.6–121.62

[56] References Cited

U.S. PATENT DOCUMENTS

| | | | |
|---|---|---|---|
| 4,298,004 | 11/1981 | Schachar et al. | 606/166 |
| 4,662,370 | 5/1987 | Hoffmann et al. | 606/166 |
| 4,665,913 | 5/1987 | L'Esperance, Jr. | 128/303.1 |
| 4,669,466 | 6/1987 | L'Esperance | 128/303.1 |
| 4,718,418 | 1/1198 | L'Esperance, Jr. | 128/303.1 |
| 4,721,379 | 1/1988 | L'Esperance | 351/212 |
| 4,724,522 | 2/1988 | Belgorod | 364/413.01 |
| 4,729,372 | 3/1988 | L'Esperance, Jr. | 128/303.1 |
| 4,732,148 | 3/1988 | L'Esperance, Jr. | 606/5 |
| 4,770,172 | 9/1988 | L'Esperance, Jr. | 128/303.1 |
| 4,773,414 | 9/1988 | L'Esperance, Jr. | 128/303.1 |
| 4,784,135 | 11/1988 | Blum et al. | 128/303.1 |
| 4,796,623 | 1/1989 | Krasner et al. | 606/166 |
| 4,856,513 | 8/1989 | Muller | 606/5 |
| 4,905,711 | 3/1990 | Bennett et al. | 128/869 |

OTHER PUBLICATIONS

Excimer Laser Surgery of the Cornea; Stephen L. Trokel, M.D. and R. Srinivasan, Ph.D. and Bodil Braren, B. A.; American Journal of Ophthalmology; vol. 96, pp. 710-715.

Corneal Surface Ablation by 193nm Excimer Laser and Wound Healing in Rabbits; Ronald N. Gaster; Investigative Ophthalmology & Visual Science, vol. 30, No. 1, Jan., 1989; pp. 90-97.

Ocular Surgery News; Jan. 1, 1989, vol. 7, No. 1, "Patent Challenge May Signal Battle for Control of Excimer Applications", pp. 1 and 3.

Primary Examiner—Stephen C. Pellegrino
Assistant Examiner—Steven J. Shumaker
Attorney, Agent, or Firm—Senniger, Powers, Leavitt & Roedel

[57] ABSTRACT

An apparatus for correcting the curvature of a cornea of an eye comprises a housing for placement on the cornea for altering the curvature of cornea to extend a portion of the cornea above a predefined plane parallel to a plane tangent to the eye. The apparatus also includes a laser which is positioned to ablate the portion of the cornea which extends above the plane from the side of the cornea. A keratometer is also included to scan the cornea to determine the amount of the cornea extending above the plane.

15 Claims, 2 Drawing Sheets

OPHTHALMOLOGICAL SURGERY APPARATUS AND METHODS

BACKGROUND OF THE INVENTION

The present invention relates to ophthalmological surgery apparatus and methods and more particularly to an ophthalmological surgery apparatus and method for distorting the shape of the cornea for removing corneal tissue to change the curvature of the cornea to correct abnormal refractive conditions.

The human eye includes two focusing elements which are the cornea and the lens. The refractive power of the cornea is expressed in diopters and regions of the cornea are assigned Keratometry (K) values in relation to their degree of curvature. The normal human cornea has a K value that ranges from 38 to 50 diopters. The sum total of all K values is constant and if the shape of the cornea is distorted the K value in one region is decreased with a corresponding increase in a neighboring region.

In order to correct for abnormal refractive errors of the eye such as myopia, hyperopia, or astigmatism, glasses or contact lenses are used. An alternative to glasses or contact lenses is surgically altering or sculpting the shape of the cornea. Corneal sculpting involves the removal of external layers of the cornea which affects the radius of curvature of the cornea. Altering the radius of curvature of the cornea increases or decreases the dioptric power of the front surface of the cornea which corrects any abnormal refractive errors.

One approach of corneal sculpting is to remove the layers of the cornea by laser ablation. Laser ablation requires using ultraviolet laser radiation to selectively ablate the anterior surface of the cornea. The laser radiation is directed perpendicular to the cornea to penetrate into the stroma. However, problems are encountered by using this head-on approach for correcting the curvature of the cornea. For example, the laser radiation may penetrate to an excessive depth in the cornea. Therefore, it would be advantageous to remove layers of the cornea by tangential laser ablation of the cornea which does not use a head-on approach. Furthermore, although micromanipulators are known in the prior art, it would be advantageous to provide a micromanipulation which can be used in combination with a tangential laser ablation.

SUMMARY OF THE INVENTION

Among the objects of the present invention is the provision of an ophthalmological surgery apparatus for surgically operating upon the outer surface of the cornea; the provision of such an ophthalmological surgery apparatus for surgically modifying optical properties of the eye through selected ablation of the outer surface of the cornea; the provision of such an ophthalmological surgery apparatus for safely applying laser radiation when surgically operating upon the outer surface of the cornea; and the provision of such an ophthalmological surgery apparatus for surgically operating upon the outer surface of the cornea from the side of the cornea.

Generally, an apparatus for correcting the curvature of a cornea of an eye comprises means for altering the curvature of the cornea to extend a portion of the cornea above a predefined plane parallel to a plane tangent to the eye and means for removing at least the portion of the cornea which extends above the predefined plane. The apparatus also includes means for determining the amount of the cornea extending above the plane.

In another form of the invention, a corneal profiling apparatus for correcting the curvature of a cornea of an eye comprises means for altering the curvature of the cornea to extend a portion of the cornea above a predefined plane parallel to a plane tangent to the eye and laser means for projecting a beam of radiation for ablating at least the portion of the cornea which extends above the plane, the laser means projecting a beam which is parallel to the predefined plane.

Other objects and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENT

Figure 1:
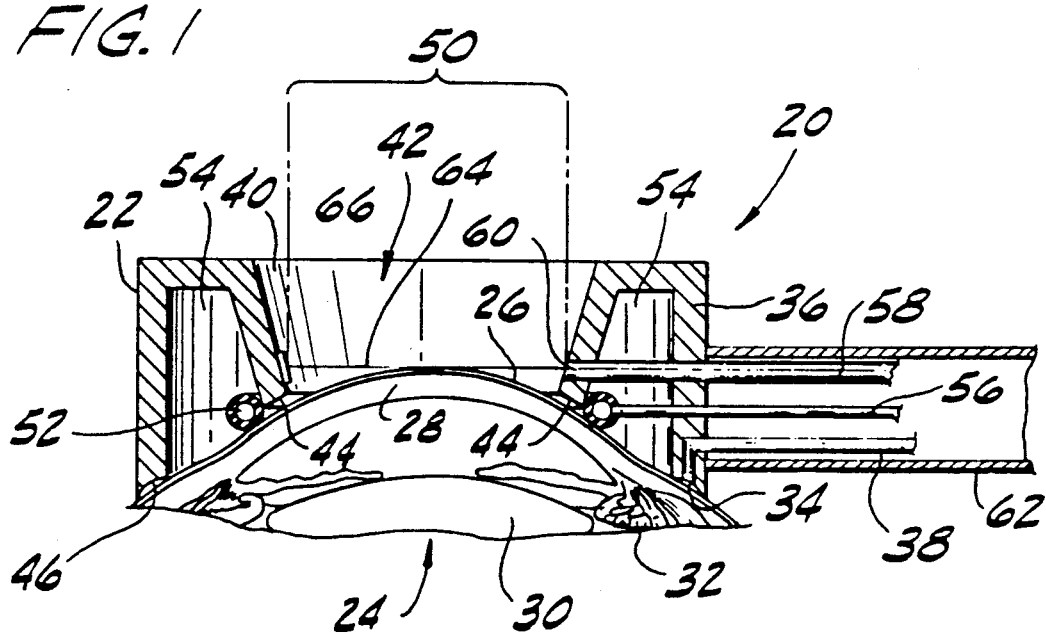
FIG. 1 is a cross-sectional view of an ophthalmological surgery apparatus of the present invention.

Referring now to FIG. 1, an ophthalmological surgery apparatus is shown indicated generally as 20 in the drawings. The apparatus 20 includes an eye retaining housing 22 which is adapted to peripherally engage an eye 24 at a corneal-scleral region 26. The eye 24 is shown to include a cornea 28, a lens 30, and an iris 32. The eye retaining housing 22 is held in place against the surface of the corneal-scleral region 26 via suction applied through a portal 34 in a side 36 of the housing 22 (see FIG. 5). The portal 34 is connected via a conduit 38 to a vacuum pump (not shown). The housing 22 comprises a hollow annulus 40 having a central opening 42. The housing 22 includes an end wall 44 contoured to engage the eye 24 via the corneal-scleral region 26. The housing 22 also includes a rim 46 including an annular channel on a bottom 48 of the housing 22. The rim 46 is contoured to engage and retain the eye 24 via the corneal-scleral region 26 when suction is applied through conduit 38. The diameter of the central opening 42 is equal to an optical zone 50 of the cornea 28. An inflatable tube 52 is positioned within a cavity 54 formed between the end wall 44 and rim 46. The tube 52 rests on the periphery of the cornea 28 and is connected to a source of pressurized air (not shown) via a conduit 56.

The housing 22 is an example of means for altering the curvature of the cornea to extend a portion of the cornea above a predefined plane parallel to a plane tangent to the eye. The tube 52 is an example of means for forcing the portion of the cornea through the central opening above the predefined plane.

An articulated arm or fiber optic cable 58 transmits radiation from a laser (not shown) to a portal 60 in the side of the housing 22. The laser is an example of means for removing at least a portion of the cornea which extends above the predefined plane. The laser selected for use preferably emits radiation in the ultraviolet range having a wavelength of 193 nm. The conduits 38 and 56 and the cable 58 are enclosed within a tube 62. Portal 60 is adjustable by using a micromanipulator 84 (see FIG. 5) which is incorporated in the apparatus 20. The typical beam dimension is 5 mm by 20 mm. To reduce the beam size, the micromanipulator is operated to reduce the size of portal 60 condense the beam size to a fine slit. The position of the portal 60 is such that the beam strikes the cornea 28 tangentially from the side. Ideally, the portal 60 is located in a plane 64 defined by the central tangent of the cornea 28 or in a plane parallel to the plane of the iris 32 when the shape of the eye is unaltered. Surface 66 is provided within the housing 22 opposite the portal 60 to absorb any excess laser radiation.

Figure 2:
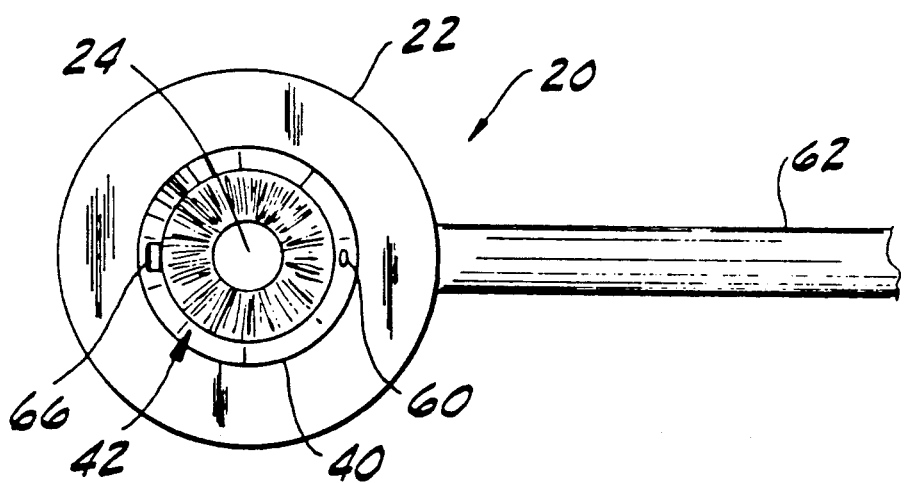
FIG. 2 is a top plan view of the ophthalmological surgery apparatus shown in FIG. 1.

A top plan view of the apparatus 20 is shown in FIG. 2. The apparatus 20 includes the central opening 42 and the annulus 40. Portal 60 is shown on one side of the apparatus 20 and the radiation absorbing surface 66 is positioned on the other side.

Figure 3:
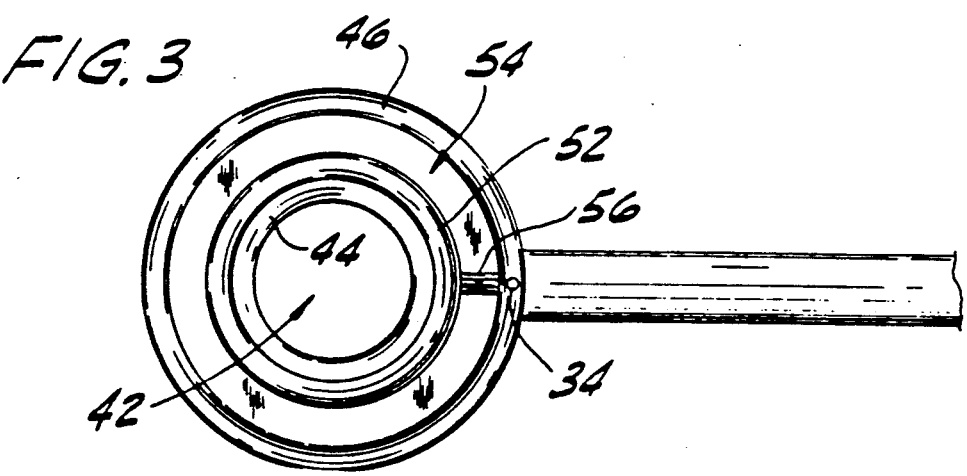
FIG. 3 is a bottom plan view of the ophthalmological surgery apparatus shown in FIG. 1.

A bottom plan view of the apparatus 20 disengaged from the eye 24 is illustrated in FIG. 3. The bottom rim 46 of the apparatus 20 includes the portal 34 which is connected to conduit 38. The bottom rim 46 contacts the cornea 28 to hold the apparatus 20 to the eye 24 when vacuum pressure is present through portal 34 and conduit 38. Tube 52 is also shown surrounding the bottom rim 46 within the cavity 54.

Figure 4:
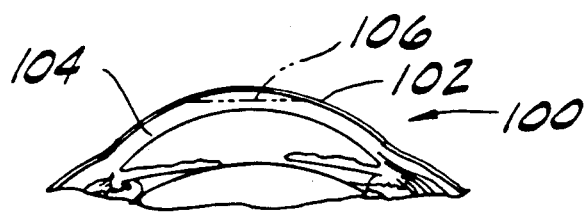
FIG. 4 is a simplified sectional view of an eye having a myoptic condition.

FIG. 4 illustrates an eye 100 wherein a myopic condition is to be corrected. Myopia is present when the curvature of the surface 102 of the cornea 104 has a radius that is too short to focus an image on the retina (not shown). A dashed line 106 represents the curvature to which the anterior surface of the cornea 104 needs to be reduced to correct the myopic condition.

In operation, the apparatus 20 is placed on the eye 24. Suction is applied through conduit 38 which causes the apparatus 20 to rest securely on the cornea 28. The inflatable tube 52 is pressurized to enlarge the tube 52 which exerts pressure on the central region of the cornea 28 to distort the eye shape and force a portion of the cornea 28 above the predefined plane 64 parallel to a plane tangent to the eye 24 (see FIG. 1). A surgical keratometer 82 scans the corneal surface and monitors the change in the shape of the cornea 28 which occurs as the pressure is increased. When the desired K value change in the center of the optical zone 50 is achieved, inflation of the tube 52 is discontinued. The keratometer 82 is an example of means for determining the amount of the cornea extending above the plane. In order to steepen the cornea 28, it may be necessary to apply pressure more centrally to the cornea 28. This is accomplished by using an insert (not shown) having a smaller centrally located opening. The micromanipulator 84 is adjusted to change the size of portal 60 depending upon the amount of stroma that needs to be ablated. For example, if a small amount of stroma needs to be ablated, the portal 60 may be adjusted by reducing both its height and its width to reduce the size of the beam ablating the stroma. If a large amount of stroma needs to be ablated, the height and width of the beam can be increased by increasing the size of portal 60 through adjustment of the micromanipulator 84.

Figure 5:
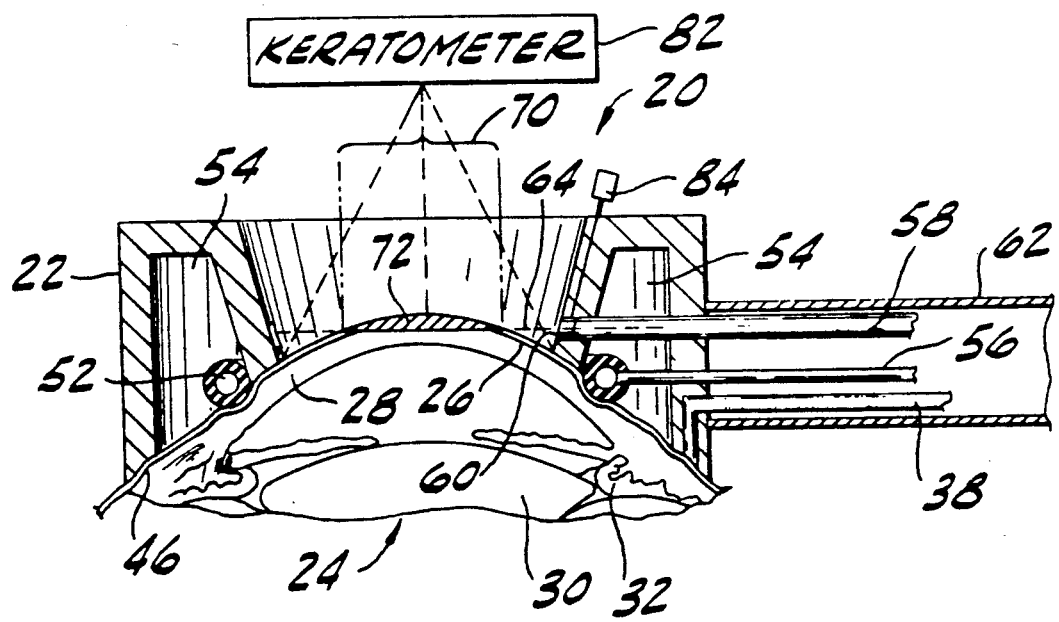
FIG. 5 is a cross-sectional view of the ophthalmological surgery apparatus with the cornea distorted by the apparatus.

The cornea 28, distorted by inflation of the tube 52, will bulge beyond the plane 64, as shown in FIG. 5. The diameter of the portion of the cornea 28 which extends beyond the plane 64 of the original cornea tangent is defined as the treatment zone 70. The diameter of the treatment zone 70 is less than the diameter of the optical zone 50 (see FIG. 1). The tissue 72 in the treatment zone 70 is ablated by the laser beam. The laser beam only ablates the corneal tissue protruding above the plane 64. The laser beam may have to be applied more than once depending upon the amount of corneal tissue or the number of layers of tissue which need to be removed to change the curvature of the cornea 28. Once the apparatus 20 is removed, the cornea 28 relaxes to its modified curvature. K value readings of the modified optical zone are taken by keratometer 82 to verify the change in refractive power has been obtained. The amount of K value measured corresponds to the amount of tissue removed. When a predictable amount of tissue is removed a predictable dioptric change will result.

In view of the above, it will be seen that the several objects of the invention are achieved and other advantageous results attained.

As various changes could be made in the above constructions without departing from the scope of the invention, it is intended that all matter contained in the above description or shown in the accompanying drawings shall be interpreted as illustrative and not in a limiting sense.

What is claimed is:

1. A corneal profiling apparatus for correcting the curvature of a cornea of an eye comprising:

means for altering the curvature of the cornea to extend a portion of the cornea above a predetermined plane parallel to a plane tangent to the eye, said means for altering including an inflatable tube positioned on the eye and means for inflating the tube thereby to change the shape of the eye and push a portion of the cornea upward; and laser means for projecting a beam of radiation for ablating at least the portion of the cornea which extends above the plane, the laser means projecting a beam which is parallel to the predefined plane.

2. The apparatus of claim 1 wherein the altering means includes a housing engaging the cornea and having a portal through which the beam passes, and further comprising means for changing a diameter of the portal thereby to change the cross-sectional size of the beam ablating the eye.

3. The apparatus of claim 1 further comprising means for scanning the cornea to determine the amount of the cornea that the altering means has extended above the plane.

4. The apparatus of claim 3 wherein the scanning means comprises a keratometer.

5. The apparatus of claim 1 further comprising means for measuring the amount of the cornea extending above the predefined plane.

6. The apparatus of claim 1 wherein the altering means comprises:

a housing for engaging the cornea, the housing including a central opening and supporting the inflatable tube, said inflatable tube forcing the portion of the cornea through the central opening above the predefined plane, when inflated.

7. The apparatus of claim 6 wherein the inflatable tube is positioned between the housing and the eye when the housing engages the cornea.

8. The apparatus of claim 7 wherein the housing further comprises a bottom rim including an annular channel in contact with a surface of the cornea and means for connecting the channel to a vacuum source thereby to create suction in the annular channel pulling the rim against the surface of the cornea.

9. The apparatus of claim 1 wherein the laser means emits radiation having a wavelength of 193 nm.

10. A method of correcting the curvature of a cornea of an eye comprising the steps of:
    altering the curvature of the cornea by inflating an inflatable tube positioned on the eye to extend a portion of the cornea above a predefined plane parallel to a plane tangent to the eye; and
    tangentially ablating by a laser at least a portion of the cornea which extends above the predefined plane.

11. The method of claim 10 further comprising the step of measuring the amount of the cornea extending above the plane.

12. The method of claim 11 wherein the measuring step comprises the step of scanning the cornea to determine the amount of the cornea extending above the plane.

13. The method of claim 12 wherein the step of inflating comprises changing the shape of the eye and pushing the portion of the cornea through a central opening in a housing.

14. A method of correcting the curvature of a cornea of an eye comprising the steps of:
    altering the curvature of the cornea by inflating an inflatable tube positioned on the eye to extend a portion of the cornea above a predefined plane parallel to a plane tangent to the eye;
    measuring the amount of the cornea extending above the plane; and
    tangentially ablating at least a portion of the cornea which extends above the predefined plane.

15. The method of claim 14 wherein the measuring step comprises the step of scanning the cornea to determine the amount of the cornea extending above the predefined plane.

* * * * *